United States Patent [19]

Nappholz et al.

[11] Patent Number: 5,172,690
[45] Date of Patent: Dec. 22, 1992

[54] AUTOMATIC STIMULUS ARTIFACT REDUCTION FOR ACCURATE ANALYSIS OF THE HEART'S STIMULATED RESPONSE

[75] Inventors: Tibor A. Nappholz, Englewood; Fred L. Vance, Parker; John W. Camerlo, Littleton; Bruce M. Steinhaus, Parker; Stephen M. Quist, Denver; Ken Koestner, Englewood, all of Colo.

[73] Assignee: Telectronics Pacing Systems, Inc., Englewood, Colo.

[21] Appl. No.: 603,988

[22] Filed: Oct. 26, 1990

[51] Int. Cl.5 .............................. A61N 1/362
[52] U.S. Cl. .............................. 128/419 PG
[58] Field of Search .................. 128/419 PG

[56] References Cited

U.S. PATENT DOCUMENTS 4,692,719 9/1987 Whigham ........................ 332/11 D
4,821,724 4/1989 Whigham et al. ............... 128/419 P Primary Examiner—Kyle L. Howell
Assistant Examiner—Scott M. Getzow
Attorney, Agent, or Firm—Gottlieb, Rackman & Reisman

[57] ABSTRACT

An apparatus adapted to be implanted in a patient for electrically stimulating the heart and analyzing the heart's stimulated response, and a method of operating the apparatus, are disclosed. The apparatus operates to reduce the stimulation polarization artifact that normally accompanies such stimulation, allowing accurate measurement of stimulated cardiac potentials. The apparatus is useful in such devices as cardiac pacemakers, tachycardia reversion devices, and defibrillators. Optimizing features are provided to allow the apparatus to function properly in noisy environments and with suboptimal leads. In addition, provision is included to make the apparatus capable of performing self-diagnosis for determining when accurate sensing is not possible.

29 Claims, 3 Drawing Sheets

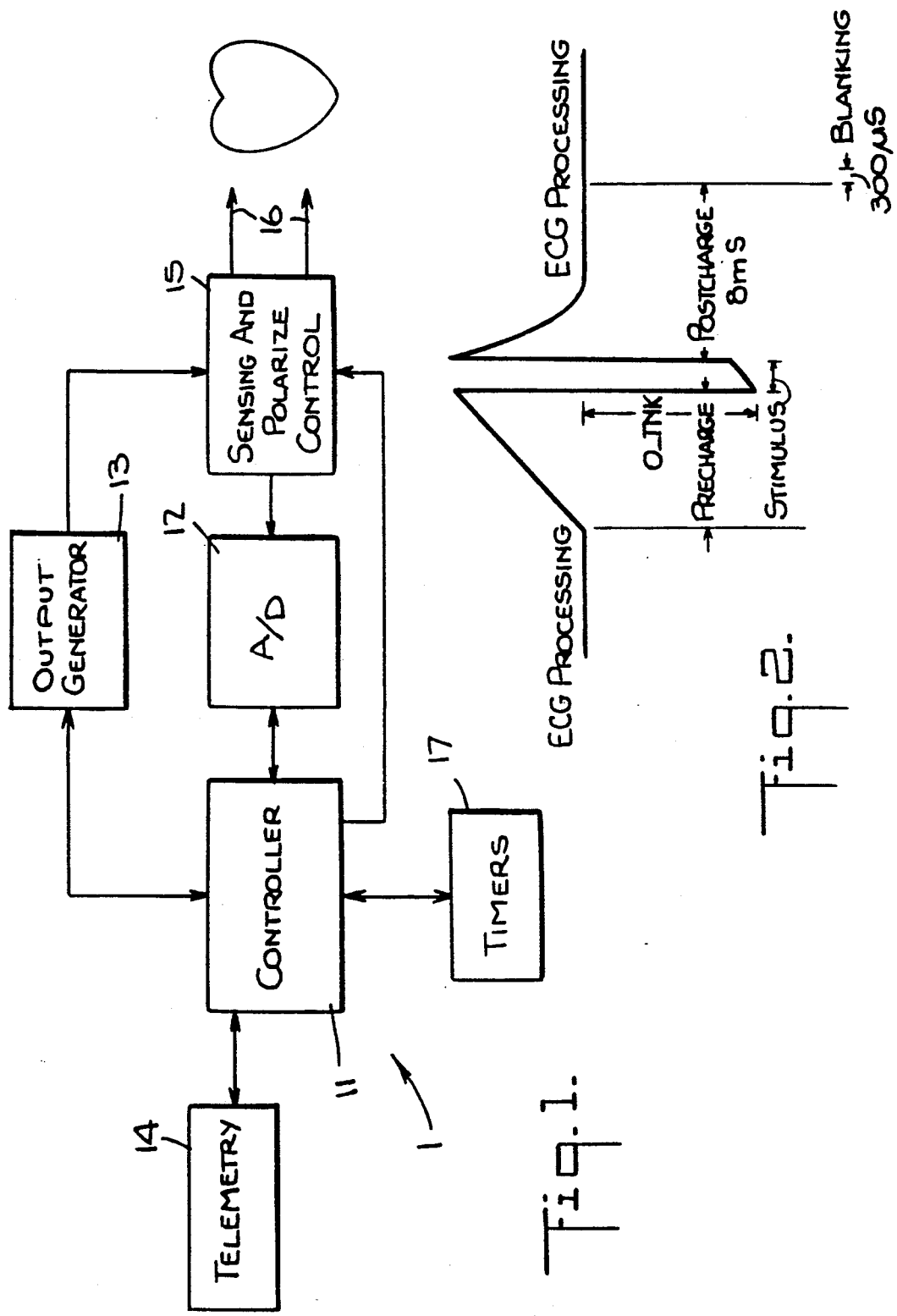

AUTOMATIC STIMULUS ARTIFACT REDUCTION FOR ACCURATE ANALYSIS OF THE HEART'S STIMULATED RESPONSE

BACKGROUND OF THE INVENTION

This invention relates to devices, including cardiac pacemakers, tachycardia reversion devices, and defibrillators, for measuring the response of the heart to an electrical stimulation very soon after the generation of a stimulus, even when the same electrode is used for stimulating and sensing. More specifically, this invention relates to such devices which are optimized to function properly in noise environments and with suboptimal leads. Furthermore, this invention relates to such devices capable of performing self-diagnoses for determining when accurate sensing is not possible.

It is desirable to accurately measure the response of the heart to an electrical stimulation pulse for a number of purposes. The initial objective for performing such measurements was the development of threshold tracking systems requiring the simple detection and distinction of a systolic event from a subthreshold non-event. More recently, stimulated response analysis has been used to control pacing rate, to detect physiological effects of drugs, and to diagnose abnormal conditions of the heart.

Stimulus polarization artifacts can interfere with the recording and analysis of the stimulated response. Consequently, there arose a need for accurate methods for eliminating the stimulation artifact and identifying the true nature of the stimulated response. The ability to automatically reduce stimulus polarization artifacts is necessary in a system which analyzes the depolarization waveform stimulated by a pulse because, in addition to generating a cardiac response, an electrical stimulus gives rise to a form of noise called the stimulus artifact. When a device generates an electrical stimulus within the heart, it creates electrical charges which are stored in the body tissues. The stimulus polarization artifact is the signal arising from the dissipation of these stored charges. The amplitude of the stimulus polarization artifact is normally so much greater than that of signals arising from a natural heartbeat or the stimulated response that it is usually futile to sense these diagnostic signals until the stimulus polarization artifact charges dissipate. This is especially true when, as in the case of the preferred embodiment of the present invention, the device uses the same electrode for stimulating and sensing.

To rapidly dissipate these charges and minimize the stimulus polarization artifact at the pacing electrode, the device generates stimulating pulses using a technique known as charge balancing. The procedure and circuit for performing charge balancing is disclosed in U.S. Pat. No. 4,821,724, entitled "Pacing Pulse Compensation", which issued on Apr. 18, 1989, and refers to the method as active recharge. This patent is assigned to the assignee of the present application and its disclosure is incorporated herein by reference. In this procedure, the device generates a triphasic stimulus, with the first and third phases being of one polarity and the second being of the opposite polarity. The amplitudes of the first and second phases are substantially proportional to each other. The third phase drives a current through the stimulating electrode until the voltage equals the starting quiescent voltage.

The charge balancing technique, as performed by the preferred embodiment of the present invention, requires circuitry for sensing cardiac electrical activity including natural polarizations, stimulated potentials and artifacts. This sensing circuitry is disclosed in U.S. Pat. No. 4,692,719, entitled "Combined Pacemaker Delta Modulator and Bandpass Filter", which issued on Sep. 8, 1987. This patent is also assigned to the assignee of the present application and its disclosure is incorporated herein by reference.

Stimulating the heart using the triphasic stimulus waveform allows the device to effectively reduce the polarization artifact, but the best balance of the three phases of the stimulation waveform is not predictable. The apparatus and method of the present invention provides a mechanism for automatically adjusting or balancing the triphasic stimulus waveform in vivo.

SUMMARY OF THE INVENTION

Briefly stated and in accordance with one aspect of the present invention, there is provided an apparatus for generating a triphasic stimulus for exciting the heart. The triphasic stimulus waveform consists of timed segments called the precharge, stimulus, and postcharge segments. The device automatically varies the duration of the precharge segment until the amplitude of the stimulation artifact is small compared to the cardiac response evoked by a stimulation pulse. To effectively separate the stimulus polarization artifact from the polarization of the heart while beating, either naturally or in response to a stimulation pulse, the apparatus introduces a stimulus and measures the subsequent segment of the intracardiac electrogram during the refractory period of the heart. This technique of stimulating and measuring the polarization during the refractory period is called refractory pulsing. The apparatus measures the intracardiac electrogram and adjusts the precharge to minimize the polarization artifact shortly after the refractory pulse.

Physiological variations in cardiac polarization during the refractory period may occur during the refractory sampling, causing the device to incorrectly set the precharge duration. The device measures the refractory samples of the intracardiac electrogram in the absence of a refractory pulse to create a template signal which compensates for such physiological variations. While adjusting the precharge duration, the device compares the refractory samples with the template to determine whether to increase or decrease the precharge duration.

In some circumstances, the device will not be capable of minimizing the stimulus artifact to a degree which will provide for safe operation of the diagnostic and control function of the device. For example, leads may become displaced or otherwise become incapable of performing properly. The apparatus performs self-diagnosis to determine when further performance of the diagnostic or control function becomes unsafe and automatically terminates that function under such conditions.

Considering the natural variability and unpredictability of biological signals, one objective of this invention is to maximize the reliability of the decision-making process of the diagnostic or control function. Consequently, the device generates the stimulus and senses the signal in a manner which optimizes the diagnostic features of the stimulated polarization waveform. The device automatically adjusts sensing sensitivity to provide the largest signal without saturation. In addition, the system adjusts the stimulation amplitude to the smallest level which will generally successfully stimulate the heart and monitors the heart response to guarantee that the heart is successfully stimulated before performing the diagnostic measurement. The automatic stimulation amplitude function insures that the device compares similar signals over time. The device also improves diagnostic reliability by performing automatic artifact reduction to minimize the size of the stimulus polarization artifact. The stimulated cardiac depolarization potential analysis methods of the present invention fit efficiently into the framework of a stimulated signal sensing and analysis system.

The above objects and advantages, in addition to others that will appear in the detailed description of the invention, will be more clearly understood by reference to the accompanying drawings, the following description, and the appended claims.

BRIEF DESCRIPTION OF THE DRAWINGS

FIG. 1 is a block diagram of an illustrative embodiment of the invention in the form of a threshold tracking stimulation apparatus;

FIG. 2 depicts the form of the triphasic stimulation pulse generated by an output generator block of FIG. 1;

DETAILED DESCRIPTION

Figure 3:
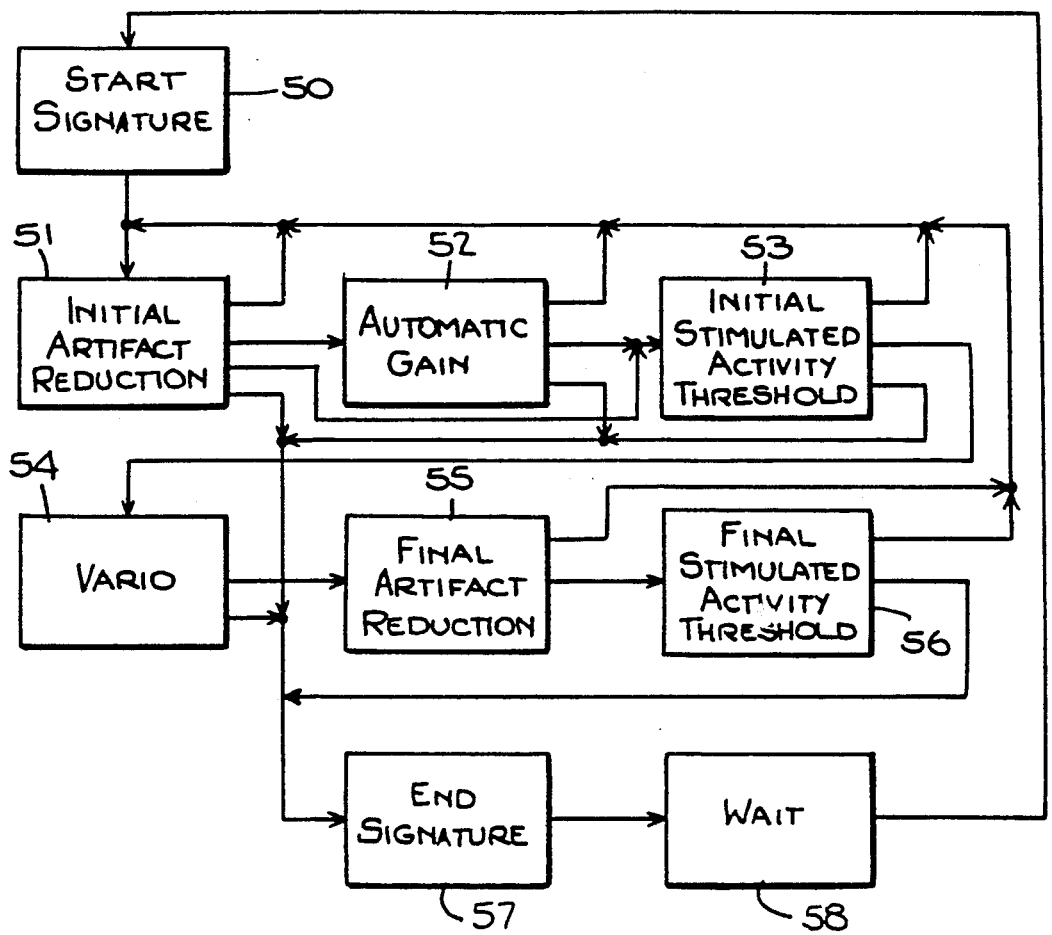
FIG. 3 is a flow chart illustrating the operational steps of stimulus artifact reduction, automatic sensitivity control, and automatic stimulus output determination performed by the illustrative embodiment of the invention.

FIG. 1 depicts, in highly symbolic block-diagram form, an apparatus, shown generally at 1, for performing automatic reduction of the stimulus polarization artifact, enabling the accurate evaluation of the electrical response of the heart. The fundamental requirements for such a device include the ability to generate and deliver, at selected intervals, electrical stimulation pulses of varying amplitudes and forms. The device must then sense the intracardiac electrogram waveform shortly after delivering a stimulus pulse and convert the waveform into a proper form for analysis. The device then analyzes the signal and from this analysis controls the amplitude and form of subsequent stimulation pulses in a manner which minimizes the stimulus polarization artifact. The device may then further analyze the electrical response of the heart, using a similar stimulation and sampling procedure, to perform such functions as automatic stimulation threshold tracking, stimulation rate control, and various procedures to diagnose malfunctions of the heart.

A controller 11 controls all of the other blocks of FIG. 1. In particular, the controller determines the amplitude and morphology of the stimulating pulse and also sets the timing of pulse delivery. The controller sets the pulse delivery parameters for the purpose of charge balancing the stimulus output. The controller also governs the timing and number of intracardiac electrogram samples in addition to determining and executing any signal filtering required for signal analysis. As the controller performs signal sampling, it carries out the analysis necessary for the diagnostic purposes of the device, as described below.

A telemetry block 14 is conventional in modern implanted cardiac pacemakers and defibrillators. It allows both adjustment of the data acquisition parameters from an external programmer and the transmission of information from the implanted apparatus to the external device. This information includes accumulated data and a signal representative of the instantaneous sensed intracardiac electrogram. Present-day sophisticated telemetry circuits allow for the interrogation of stored diagnostic data and the derivation of real-time operational data.

The apparatus uses a form of delta modulation to produce a digital signal for analysis by controller 11. An analog-to-digital block 12 is provided with a signal called ANGL_CMP from a sensing and polarization controller 15. The ANGL_CMP signal is a two level waveform representing the sensed signal as a sequence of bits indicating the time history of increases and decreases in the signal amplitude. The analog-to-digital block 12 converts the bit sequence into a form which the controller can read to perform the functions of sensing and intracardiac electrogram acquisition. The output signal of the analog-to-digital block 12 tracks the input signal in the sense that the output represents a 1 value when the input is increasing and a 0 value when the input is decreasing.

The controller 11 has a direct connection for controlling the sensing and polarization controller 15. The sensing and polarization controller has control circuits for performing data acquisition and pulse generation. To control sensing sensitivity, the controller 11 writes commands into the sensing and polarization controller 15 to adjust an 8-bit register which, in turn, sets each of eight switches within a resistor network circuit to an open or closed condition.

Control words written from the controller 11 to the sensing and polarization controller 15 determine the configuration of its sensing and stimulation circuits. The device delivers a negative polarity stimulus through that conductor of a lead 16 which has an electrical connection to the tip electrode of the lead. Other electrode connections of apparatus 1 are its case (the electrical connection is with the physical case of the device) and the ring electrode of lead 16. The device may connect in either a unipolar or bipolar fashion to lead 16. When connected in a unipolar mode, the active electrode is at the lead tip, which is in contact with the cardiac tissue to be stimulated, and the indifferent electrode is the case of the implanted device. When connected in a bipolar mode, the indifferent electrode can be either the case or the ring electrode, which is an annular electrode on the lead a short distance from the tip electrode. A command code written by the controller 11 determines the settings of switches to determine which electrode is active and which is indifferent during stimulation as well as sensing. The code may specify a different switch setting during stimulation as compared to sensing. Switch settings determine the operative configuration of the device: bipolar, unipolar tip-case or unipolar ring-case. Unipolar signals, arising from cardiac potentials accumulated over a larger surface of the ventricle, generally contain more information than bipolar signals, providing a more reliable diagnostic result. On the other hand, bipolar signals offer better rejection of noise, including muscle and motion artifacts, and provide the most detailed signal description of the electrophysiological state from a localized region of the ventricle. Control bytes written by the controller 11 to the sensing and polarization controller 15 determine the setting of other switches to accomplish the tasks of various modes of stimulation and sensor measurement acquisition. These switch settings are described in detail in the aforesaid U.S. Pat. No. 4,821,724.

An output generator 13, in response to control bytes written by the controller 11, prepares for stimulation by storing electrical charge on capacitors and delivers the stimulating pulses, as described in said U.S. Pat. No. 4,821,724. Control bytes written to the output generator by the controller 11 determine the amplitudes, polarities and durations of the phases of the pacing stimulus pulses. Referring to FIG. 2, wherein a pacing stimulus pulse is illustrated, the pacing stimulus pulse includes four periods or zones, called precharge, stimulus, postcharge, and blanking. It is to be understood that the waveform of FIG. 2 is not drawn to scale. The controller 11 determines the duration of the precharge period, the postcharge interval duration (typically about 8 milliseconds), and the width of the negative portion of the stimulus pulse (usually in the range of 0.1 to 1.0 and commonly 0.5 milliseconds). After the stimulus pulse, the output generator times a blanking interval of about 300 microseconds to allow the circuit to settle after stimulation. The waveform of FIG. 2 represents the potential between the conductors of the lead 16 of FIG. 1. One objective of the invention is for the controller to set the amplitudes and durations for these four periods in a manner to minimize the stimulation polarization artifact at the tip or pacing electrode, providing reliable sensing of the heart's stimulated potential resulting from a generated pulse.

For a particular implanted lead, the controller 11 can adjust the precharge period to minimize the after-potential at the pacing electrode following the 8 millisecond postcharge duration. The precharge duration ranges from 0 to about 4 milliseconds. A typical precharge period is about 3 milliseconds when using an 8 millisecond postcharge interval. The device uses an arbitrarily selected postcharge duration of 8 milliseconds, since this is sufficiently short to permit sensing of the stimulated potential.

The controller 11 writes set-up and duration information to a timer 17. The timer 17 responds to this information by generating wake-up signals to the controller after the designated time expires. The controller uses timer wake-ups to govern the timing of cardiac cycles as well as to time short-term intervals for miscellaneous operations including the setting of timing for intracardiac electrogram sampling. In addition, the controller uses timer wake-up signals to control a real-time clock function for determining the length of time since manufacture of the device and for initiating long-term housekeeping functions. When the controller, in conjunction with the real-time clock signal, determines that a measurement and analysis session is due, it begins a measurement procedure illustrated in FIG. 3.

FIG. 3 is a flow chart illustrating a procedure for measuring the stimulated potential, reducing the polarization artifact, setting sensing sensitivity (gain), and determining the minimum stimulation amplitude for safely activating the heart in the illustrative embodiment of the invention. Although the stimulus duration remains constant throughout the procedure in this embodiment of the device, it is to be understood that varying either or both the stimulus duration and amplitude to adequately stimulate the heart is considered to be within the scope of this invention. Although the external programmer may set the configuration of the device to stimulate and sense signals on the lead 16 in either the unipolar or bipolar modes, the selected mode should remain constant throughout the procedure of FIG. 3.

When a device is performing cardiovascular monitoring or control operations, the best results are accomplished when the polarization artifact is optimally reduced to a level that is small in comparison to sensed stimulated potentials and intrinsic cardiac events. Using some leads, a directly recorded tip intracardiac electrogram does not produce suitable signals for analysis no matter how the stimulation parameter settings are programmed, unless the device minimizes the polarization artifact. This procedure may be called charge balancing because its goal is to determine a combination of charges delivered in the two positive phases and the single negative phase of the stimulus waveform which results in an acceptably small polarization artifact.

The polarization artifact reduction procedure of FIG. 3 includes nine sub-procedures: start signature 50, initial artifact reduction 51, automatic gain 52, initial stimulated activity threshold 53, vario 54, final artifact reduction 55, final stimulated activity threshold 56, end signature 57, and stimulated potential sampling 58. In the eight sub-procedures (50 to 57), the device performs polarization artifact reduction and automatically adjusts the sensing amplifier gain and the stimulus pulse amplitude. We refer to these first seven sub-procedures as the polarization artifact reduction procedure. In the stimulated potential sampling 58 sub-procedure, the device performs a stimulated response analysis procedure for stimulation threshold tracking, automatic rate responsiveness, or various methods for diagnosing abnormal heart activity.

The controller 11 performs the polarization artifact reduction procedure, beginning with the start signature 50 sub-procedure, when any of the following events occur: a system hardware or software reset, an authorized external device sends a "start procedure" command using telemetric communication, an internal timer set to periodically restart the procedure times out, or the delivered stimulus fails to stimulate a response by the heart in three consecutive stimulus cycles.

In addition to reducing the polarization artifact, the procedure of FIG. 3 addresses fusion events, another problem creating difficulties when attempting to accurately measure stimulated cardiac signals. Fusion events are natural cardiac depolarizations occurring simultaneously with at least some portion of the stimulated potential polarization which changes the morphology of the sensed intracardiac electrogram signal. The preferred embodiment of the invention addresses fusion problems by elevating the cardiac stimulation rate to a level higher than the natural rate. When the event initiating the polarization artifact reduction procedure occurs, the controller performs initialization operations. In the usual operation of the cardiac stimulation device, when the device is not performing the polarization artifact procedure, software continuously updates an average of cardiac cycle interval lengths (stimulated or sensed). The preferred embodiment of the invention determines a weighted running average of interval lengths by adding the current interval to three times the running average and dividing this result by four. Determining the average in this manner is economical in terms of memory and current usage. Upon the event initiating the procedure, software converts the aforesaid running average interval into a rate and begins overdriving the average rate by a predetermined overdrive increment (for example, 25 bpm), but limiting the rate to a programmed maximum. The device continues to pace at this overdrive rate for the entire polarization artifact reduction procedure which endures, for example, for two to three minutes. To prevent the device from constantly boosting the rate in a positive feedback loop, it discontinues the updating of the running average of cardiac interval durations whenever it is overdriving the natural rate.

The purpose of the start signature 50 sub-procedure is to provide notification to anyone monitoring the cardiac signal that the device is beginning an operation which will automatically alter important stimulus parameters. Normally, a cardiac stimulation device generates a stimulus once each cardiac cycle (unless the heart beats naturally in a timely manner) upon the time-out of an internal timer. In the start signature 50 sub-procedure, the device provides the notification operation by generating a second pulse shortly after the stimulus. The time interval between pulses (for example, 75 msec) is sufficiently short so that the second pulse is within the refractory period, when it cannot stimulate the heart muscle. The paired pulses are called signature pulses. If the event initiating the polarization artifact reduction procedure is the periodic time-out of the internal timer, then the amplitude of the signature pulses is the value determined in the last threshold search operation, the stimulation threshold plus a safety margin predetermined to insure that the stimulus will normally generate a response. If any other event starts the procedure, the signature pulse amplitude is 7.5 V.

In the preferred embodiment of the invention, if the amplitude of the signature pulse delivered in block 50 of FIG. 3 is 7.5 V, then the controller 11 sets the stimulus pulse amplitude to 3.75 V for the initial artifact reduction 51 sub-procedure to be described. This reduction in amplitude is necessary due to the difficulty in reducing the stimulation polarization artifact at high pulse amplitudes. If the signature pulse amplitude is the stimulation threshold plus a safety margin, the controller continues to generate this amplitude for subsequent pulses.

After delivering the signature pulses, the controller performs the initial artifact reduction 51 sub-procedure. The procedure also enters initial artifact reduction 51 if the stimulation amplitude is determined by the vario 54 operation, hereinafter described, and this stimulation fails to evoke a cardiac response for three consecutive stimulation cycles while the device is operating in one of the sub-procedures following initial artifact reduction but prior to end signature 57. The procedure also recycles to the beginning of the initial artifact reduction 51 sub-procedure upon a single non-consecutive residual artifact test failure (this test is discussed below) during either artifact reduction sub-procedure (51 or 55).

The purpose of residual artifact reduction is to distinguish polarization artifact from stimulated cardiac depolarizations and to eliminate or reduce the amplitude of the artifact. The device does this by generating a stimulating pulse during the absolute refractory period of the heart.

When the cardiac cycle timer expires, the device delivers a stimulus to cause a heart beat then samples the intracardiac electrogram of the stimulated response and calculates activity to determine whether the stimulus successfully stimulated the heart. "Activity" is the measurement of the heart response. In the preferred embodiment of the invention, software determines activity by sampling the output signal of the analog-to-digital block 12 (of FIG. 1) every four milliseconds following the blanking period after the stimulus generation, and continues to sample for a sufficient period of time for the heart's response to be detected. The controller 11 synchronizes the timing of the samples to the trailing edge of the negative phase of the stimulation pulse, with the first sample taken at the first multiple of four milliseconds which occurs after the blanking period. To determine activity, software acquires and digitally double integrates six samples. In the preferred embodiment of the invention, the samples are in the form of delta modulator values or readings, in accordance with U.S. Pat. No. 4,692,719, mentioned earlier herein. These delta modulator values are measurements of the sensed signal amplitude difference between a current sample and a previous sample. The double integration procedure requires the accumulation of two sums, the first integral sum and the second integral sum which software initializes to zero before the first sample following the stimulus pulse. Software produces the first integral sum by adding the value of the current sample to the sum of the previous samples. Software derives the second integral sum by adding the value of the current first integral sum to the sum of the previous first integral values. The final double integral summation value represents the activity of the heart's response to the stimulation pulse. When the activity value exceeds a predetermined value, it indicates the occurrence of a responsive heartbeat. The result of the first integration reconstructs the time waveform of the intracardiac signals and the result of the second integration expresses the area under the waveform curve.

Figure 5:
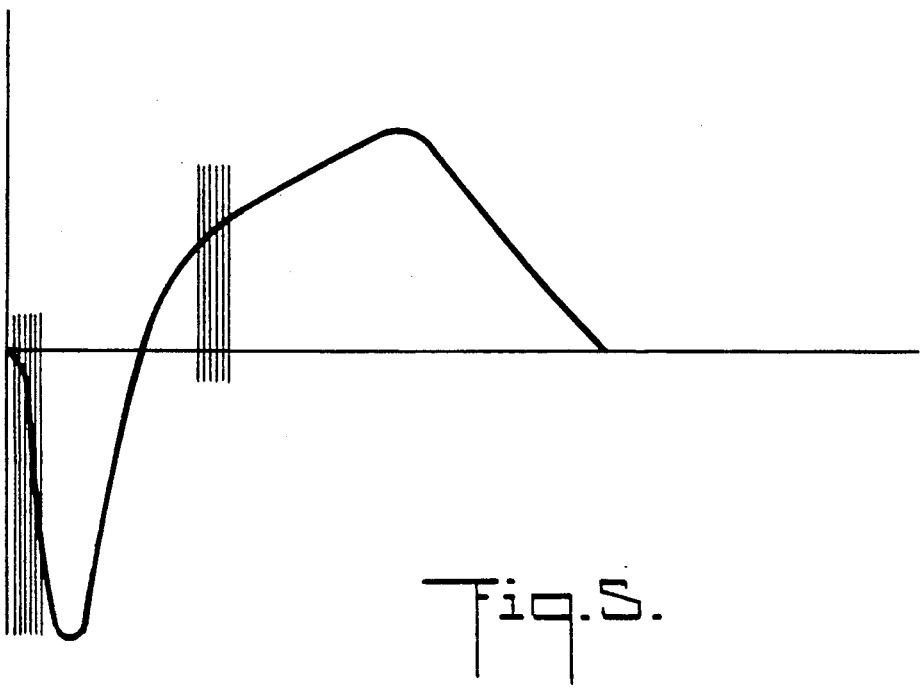
FIG. 5 is a sample illustration of a stimulated intracardiac electrogram QRST-complex waveform as sampled and measured by the apparatus during the template acquisition sub-procedure.
Figure 6:
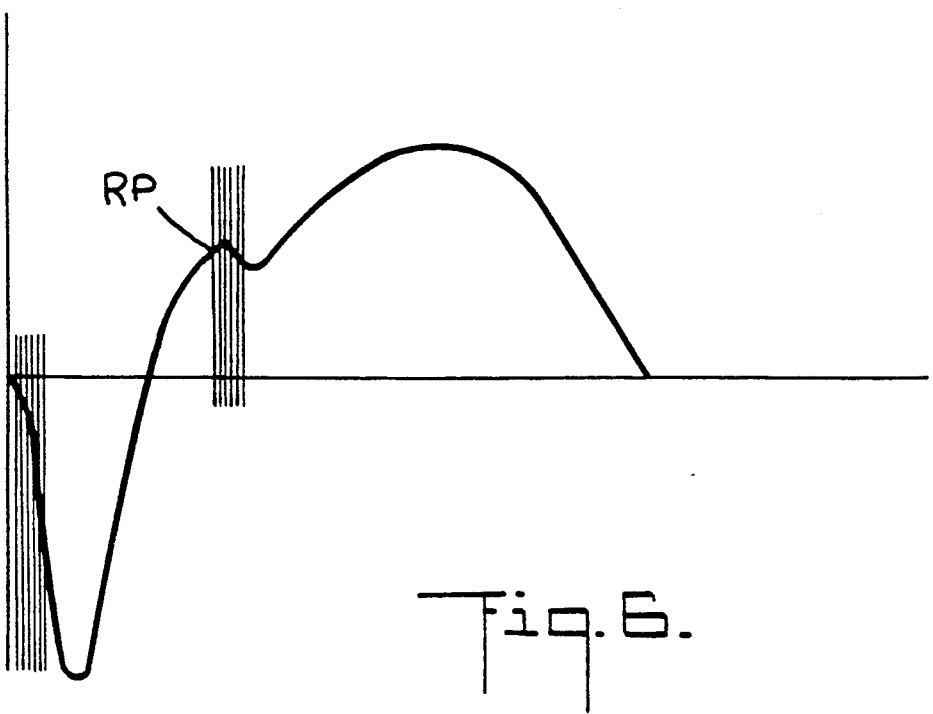
FIG. 6 is a sample illustration of a stimulated intracardiac electrogram QRST-complex waveform as sampled and measured by the apparatus during a stepwise artifact reduction sub-procedure.

Signals sampled using bipolar sensing may display a biphasic morphology within the six samples. Unipolar signals are typically monophasic and negative. The Q-S width portion of FIG. 5 and FIG. 6 illustrate this difference. Double integration samples acquired when the sensing circuits are configured in the bipolar mode would be too inaccurate for clinical usage. Accordingly software accumulates the absolute value of the intermediate sum into the final sum while performing in the bipolar sensing mode. Since signals measured when circuits are configured in the unipolar configuration nearly always have a negative polarity, software reverses the sign of the intermediate integral sums before accumulating the second integral sum. If such a result is negative in sign, software sets it to zero.

Software compares the activity to a stimulated activity threshold value derived in the most recent stimulated activity threshold operation (53 or 56 of FIG. 3). (If no stimulated activity threshold operation has taken place under the current stimulation conditions, the controller may initialize the stimulated activity threshold value to a low magnitude, even zero, to guarantee that the procedure will not fail unnecessarily when the value is not known.) If activity is greater than the stimulated activity threshold value, software determines that the pulse successfully stimulated the heart. If the pulse does not stimulate the heart, any further data analysis for the current cardiac cycle ends. It is possible that the low activity value may actually indicate a fusion event rather than a failure to stimulate the heart. Since the device can avoid the problems arising from fusion events by further overdriving the pacing rate, it responds to the detected failure to stimulate the heart by increasing the pacing rate by 15 bpm for a single failure and by 10 bpm more to a total of 25 bpm for the second of two consecutive failures. Software limits the overdrive rates to the programmed maximum. To prevent the device from failing to sense a subsequent natural heartbeat after a single failure, the device begins sensing after a short delay following the determination that the heart did not respond to the stimulus. In the case of either two or three consecutive failures, the device issues a backup stimulation pulse soon after the last of such inadequate stimulus pulses (about 125 msec). The backup stimulus has twice the pulse duration of the original stimulus to sustain the patient in case the patient's health is dependent on such stimulation. If the stimulus fails to activate the heart on three consecutive cycles, the operation of the procedure either restarts the initial artifact reduction 51 sub-procedure if this is the first failure within an artifact reduction procedure, or terminates the procedure by delivering the end signature pulses in block 57 if this is the second such failure. The device responds to the failure to stimulate the heart in this manner for all sub-procedures of the artifact reduction procedure, except that the method for the vario 54 sub-procedure differs slightly, as will be described below.

Upon successful stimulation of the heart, the device delivers an additional pulse, called a refractory pulse, during the heart's refractory period (for example, about 125 ms after the stimulus pulse). By generating this pulse during the absolute refractory period, after which any signal sensed is due primarily to polarization artifact, the device distinguishes the polarization artifact from either stimulated or natural cardiac depolarizations. Following the refractory pulse, the device performs two sampling operations of the polarization artifact signal. In the first sampling operation, software performs residual artifact sampling after the trailing edge of the refractory pulse using the same sampling procedure (six samples acquired at four millisecond intervals) as was performed while determining the activity following the stimulus pulse. In the second sampling operation, the device measures the polarization artifact to derive an artifact reduction parameter. Software performs an artifact reduction parameter accumulation on the first two or three samples acquired during the first sampling operation, in a manner similar to that done in connection with the double integration to derive the activity, except that the artifact reduction parameter accumulation persists for two or three samples rather than six and the second summation accumulates the intermediate sum without changing the sign of the first integral of the signal. Experimentally, these two or three samples were shown to characterize the peak amplitude of the first phase of a typically biphasic polarization artifact for the purpose of performing adjustments to reduce this artifact as will appear in greater detail below.

Figure 4:
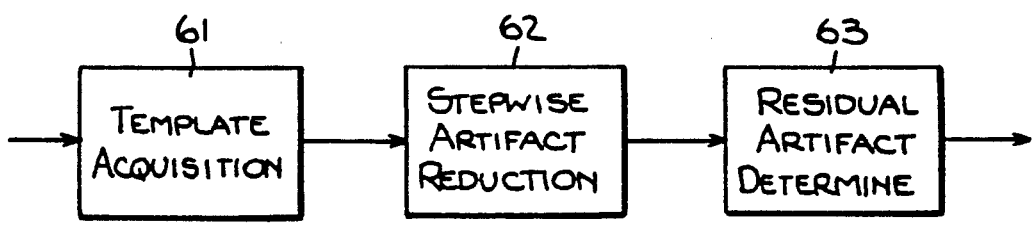
FIG. 4 is a flow chart illustrating the operational steps of the stimulus artifact reduction function performed by the illustrative embodiment of the invention.

In both artifact reduction sub-procedures (51 and 55), the controller 11 performs the operations, shown in FIG. 4, of template acquisition 61, stepwise artifact reduction 62, and residual artifact determination 63.

During template acquisition 61, the controller measures the underlying intracardiac electrogram signal detected during refractory sampling in the absence of a refractory pulse. The purpose of stepwise artifact reduction 62 is to automatically adjust the precharge duration of the triphasic stimulus waveform in vivo, in a small step within each cardiac cycle, to eliminate or reduce the polarization artifact. The device varies the precharge duration until the polarization artifact is small in comparison to the ventricular stimulated response. In the residual artifact determination 63, software corrects the intracardiac electrogram signals measured following a refractory pulse to remove therefrom the underlying intracardiac electrogram signals which were sampled during template acquisition 61. Software then uses the resulting residual artifact parameter for device self-diagnosis and control as will appear in greater detail below.

In the first task of the template acquisition 61 operation, the controller initializes the precharge duration to the value determined in the most recent successful initial or final artifact reduction sub-procedure. Software run by the controller performs this task only if the stimulus pulse amplitude is 3.75 V. If the stimulus pulse amplitude is the previously determined stimulation threshold plus margin value, the device is performing the polarization artifact reduction procedure for the purpose of maintenance rather than because of a form of system failure and there is no reason to change the precharge duration in a properly functioning system. Following this initialization task, the stimulus pulse amplitude and precharge duration remain unchanged throughout the template acquisition 61 and the stepwise artifact reduction 62 operations. To allow the controller to measure the underlying electrogram signal occurring during the sampled portion of the heart's refractory period, it sets the refractory pulse amplitude to zero volts for template acquisition 61. The precharge duration for the refractory pulse is the same as that for the stimulus pulse. Template acquisition 61 lasts for eight cardiac cycles, during which software measures and accumulates samples of the underlying intracardiac electrogram signal during both the aforesaid six sample sampling operation to create a residual artifact template for correcting the residual artifact signal, and during the two or three sample sampling operation to create an artifact reduction template which is necessary for performing stepwise artifact reduction. The templates are created by summing and averaging the double integral values obtained during the eight cardiac cycles.

FIG. 5 illustrates a typical stimulated intracardiac electrogram waveform as detected by the device sensing in the unipolar mode during the template acquisition operation. (During template acquisition, the refractory pulse amplitude is zero volts). Vertical lines on the waveform indicate times at which the apparatus performs sampling operations. During the first group of six samples, the device ascertains whether the stimulation pulse successfully evoked a response from the heart. During the second group of six samples, the device averages (for eight cardiac cycles) the integral of the first three samples to determine the artifact reduction parameter template and averages the integral of all six samples to determine the residual artifact template.

During stepwise artifact reduction 62, while generating both the stimulus and the refractory pulses using the triphasic waveform of FIG. 2 (precharge, stimulus, and postcharge), the device 1 varies the precharge duration until the refractory polarization artifact is small in comparison to the ventricular stimulated response. The controller sets the pulse amplitude for the refractory pulse to 2.5 V if the stimulus pulse amplitude is 3.75 V, otherwise the device maintains a refractory pulse amplitude of stimulus threshold plus margin (the same amplitude as for the stimulus pulse). A stimulus pulse amplitude of 3.75 V implies that the threshold stimulus pulse amplitude is not known. Since the threshold stimulus pulse amplitude may range from 3.75 V down to 0.5 V or lower and the precharge duration which minimizes the polarization artifact varies nearly proportionally to the stimulus pulse amplitude, minimizing the polarization artifact starting from a refractory pulse amplitude of 2.5 V will provide a mid-range precharge duration to best reduce the artifact throughout the range of amplitudes which will be spanned in the subsequent vario 54 operation.

The device 1 samples and accumulates the artifact reduction parameter for each cardiac cycle and subtracts the artifact reduction template from the artifact reduction parameter, then adjusts the precharge duration by about 30 usec in the direction of the sign of the subtraction result. Because the polarization artifact represents a sensing amplifier's (not shown) response to an offset voltage (polarization) on the lead electrodes, the controller 11 uses the polarity of the first phase of the artifact to determine which direction to change the precharge duration for the refractory pulse to further reduce the artifact amplitude. The precharge duration of the stimulus pulse remains unchanged at this time. The controller increases the precharge duration if the first phase of the polarization artifact is positive, otherwise it decreases the duration. The output generator 13 and the sensing and polarization controller 15 are designed to function properly in combination with a wide variety of leads 16. Leads are constructed from many types of materials and have very different electrical characteristics (for example, impedances). An excessively large or small precharge duration value may create a large artifact which the artifact reduction operation 62 of FIG. 3 cannot reduce. For this reason, software imposes predetermined upper and lower limits on precharge duration. The value of these limits is based on electrical characteristics of the circuits and leads. If the controller attempts to increase the precharge duration above the upper limit or decrease the precharge duration below a lower limit (this is usually zero usec), then the stepwise artifact reduction operation 62 finishes. While the device is performing the stepwise artifact reduction step within the prescribed limits, at some point further changes in precharge duration will either completely eliminate the polarization artifact or cause it to reverse polarity, depending on the sensing amplifier gain, stimulus energy, and characteristics of the electrode system. A polarization reversal occurs when the change in precharge duration causes the result of the subtraction to change in sign as compared to the result of the previous cycle. After a predetermined number of polarization reversals (for example, four), the controller determines that the polarization artifact is sufficiently reduced and the sub-procedure sequences to the residual artifact determination 63. The device requires a number of polarization reversals to provide protection against incorrectly determining the proper precharge duration in the presence of fusion events. Because some leads produce only a very minor polarization artifact for the procedure to eliminate, the controller also terminates the stepwise artifact reduction operation 62 if the sub-procedure endures longer than a predetermined number of steps (for example, 128). The precharge duration resulting from the residual artifact determination operation is the optimum precharge duration.

FIG. 6 illustrates a stimulated intracardiac electrogram waveform, similar to that of FIG. 5, after the device has increased the refractory pulse amplitude for the stepwise artifact reduction operation from the zero voltage of FIG. 5 to the refractory pulse amplitude for stimulus polarization artifact reduction discussed two paragraphs earlier herein. The refractory pulse occurs at point RP in FIG. 6 and this results in the perturbation of the waveform following the refractory pulse. This perturbation is an example of the stimulus polarization artifact. Its amplitude and duration depend on the precharge duration, among other factors as discussed earlier. As shown, the three artifact reduction parameter samples are taken during the early part of this stimulus polarization artifact. After acquiring the three samples, the device 1 performs stepwise artifact reduction by adjusting the precharge duration value, in the manner described in the preceding paragraph.

In the residual artifact determination 63 operation which occurs for eight cardiac cycles following the stepwise artifact reduction 62 operation, the controller 11 first sets the precharge duration of both the stimulus and the refractory pulses to the newly determined optimum precharge duration. The controller maintains the same stimulus and refractory pulse amplitudes in the transition from the stepwise artifact reduction to residual artifact determination. For the eight cardiac cycles of the residual artifact determination 63, software measures and accumulates only the residual artifact value (not the artifact reduction parameter). On the eighth cardiac cycle, the controller divides the accumulated residual artifact by eight and subtracts from it the residual artifact template determined by the previous template acquisition operation 61. This result is the template-corrected residual artifact. In the final operation of the residual artifact 63 operation, the controller saves the optimum precharge duration in memory for usage in future residual artifact reduction operations in case the procedure restarts for a reason other than timed recycling.

Physiological or external noise (for example, 60 cycle noise) is one phenomenon which may influence the operation of the artifact reduction procedure. The device detects such noise by measuring intracardiac electrograms during the heart's relative refractory period. For each sensed signal with an amplitude change greater than a predetermined sensing threshold during the relative refractory period of a cardiac cycle, the controller restarts the refractory period timer and increments the sensing threshold for the remainder of that cardiac cycle. The new sensing threshold endures until a sensed signal greater than such new sensed threshold occurs and restarts the timer and again increments the sensing threshold. After the refractory timer has timed out and prior to the timing out of the cardiac cycle timer, sensed signals inhibit the device from generating stimulus pulses. Once the refractory timer extends beyond the cardiac cycle timer, a sensed signal can no longer inhibit the device from delivering a stimulus pulse. A noise cycle is defined as a cardiac cycle in which the refractory timer extends beyond the cardiac cycle timer due to refractory period recycling. When the device detects a noise cycle, software always suspends the sampling function of the polarization artifact reduction procedure for that cardiac cycle. Because overdriving to elevate the heart rate occurs during this procedure and noise cycle sensing may cause the device to remain in an overdriven state potentially forever, the controller accumulates a noise cycle counter. If noise cycle counter accumulates a count of 256 during a single artifact reduction procedure encompassing blocks 51 and 55 of FIG. 3, the controller jumps to the end signature 57 operation and terminates the procedure, restoring the stimulus pulse amplitude and precharge duration to the results of the most recent successful polarization artifact reduction procedure.

Again referring to FIG. 3, after the successful completion of the initial artifact reduction 51, the controller performs the automatic gain 52 sub-procedure only if an external programmer activates an automatic gain function. When enabled, the automatic gain function procedure sets the gain of the sensing amplifier in the sensing and polarization controller 15 by analyzing samples acquired during the absolute refractory period. The automatic gain 52 sub-procedure sets gain so that sensed signals will have a high amplitude, but not so high as to produce saturated signals. Setting the gain in this manner improves the device's natural heartbeat signal sensing operation as well as its signal analysis capabilities while performing the other sub-procedures of FIG. 3. If the automatic gain function is disabled and an automatic stimulus pulse amplitude function is enabled, control of the procedure proceeds to the initial stimulated activity threshold 53 sub-procedure. When enabled, the automatic stimulus pulse amplitude function allows the device 1 to determine a stimulated activity threshold value which, when sensed and measured, indicates the successful stimulation of the heart and the stimulus threshold pulse margin amplitude value necessary to successfully stimulate the heart, as will be described in detail hereinafter. If neither the automatic gain nor the automatic stimulus pulse amplitude function is enabled, control of the procedure jumps to the end signature 57 sub-procedure.

During automatic gain 52 sub-procedure, the device 1 samples the activity of the intracardiac electrogram and responds to the failure to activate the heart in the manner described previously. If the device successfully activates the heart, it continues to sample the intracardiac electrogram for additional samples. The stimulus pulse amplitude for the automatic gain 52 sub-procedure is the same as the amplitude of the stimulus pulse in the initial artifact reduction 51 operation. The term "stimulated potential signal" is intended to refer to signals generated by the heart during the heart's activation wave in response to a stimulated pulse applied to the heart. It primarily refers to the heart's responsive QRS-complex. The total number of samples is intended to encompass the entire stimulated potential signal, including the QRS-complex. The number of samples taken depends on the bandwidth of the sense amplifier in the sensing and polarization controller (block 15 of FIG. 1). The device 1 measures each of the stimulated potential signal samples to find the largest positive value in four consecutive paced cardiac cycles. On every fourth cardiac cycle, if the largest positive sample is less than or equal to a predetermined automatic gain test level of amplitude, then the device increases the gain setting in the sensing and polarization controller by one count. Otherwise, the controller 11 decreases the gain setting by one count. To prevent a potentially unsafe sensitivity setting, the controller 11 limits the gain setting to predetermined maximum and minimum values. If updating the gain would violate either limit, the gain setting remains the same. In either case, the software tests the current amplitude test result against the amplitude test result from the previous four cycle sample. If the largest positive value from the current sample is greater than the automatic gain test level of amplitude and the largest positive value from the previous sample is not, the condition is an automatic gain amplitude test crossing. Upon the occurrence of a predetermined number of automatic gain amplitude test crossings, the automatic gain 52 sub-procedure finishes and, if the external programmer has activated the automatic stimulus pulse amplitude function, control of the procedure moves to the initial stimulated activity threshold 53 sub-procedure. If the automatic stimulus pulse amplitude function is disabled, control of the procedure jumps to the end signature 57 sub-procedure.

The purpose of the stimulated activity threshold operation is to measure the "stimulated activity threshold value", which is defined as the activity which distinguishes a stimulation pulse amplitude normally capable of generating a response by the heart from the activity of a stimulation pulse amplitude which does not. The stimulus pulse amplitude for the initial stimulated activity threshold 53 sub-procedure is the same as the amplitude of the stimulus pulse in the previous operation (either the initial artifact reduction 51 or automatic gain 52 sub-procedure), except that software limits the amplitude to a value of the maximum allowable stimulus threshold plus the margin (for example, 3.2 V). During the stimulated activity threshold sub-procedure, the controller measures the activity by sampling and double integrating in the manner described previously, then averages the activity for eight successfully sampled cardiac cycles. During a stimulated activity threshold sub-procedure, the device samples the activity of the intracardiac electrogram and responds to the failure to activate the heart in the manner described previously, with one exception. A failure to stimulate the heart in three consecutive cardiac cycles indicates that the stimulus threshold amplitude is greater than the aforesaid maximum allowable stimulus threshold plus margin. If the stimulus pulse amplitude is less than such threshold plus margin, then the controller 11 restarts the procedure by initializing the stimulus pulse amplitude to 3.75 V and looping back to the initial artifact reduction 51 operation. Otherwise, software terminates the procedure by setting the stimulus pulse amplitude to a safe level (for example, 7.5 V) and jumping to the end signature 57 sub-procedure.

After measuring the averaged activity for the eight cycles referred to above, software performs a residual artifact test by comparing the magnitude of the corrected stimulated activity (the averaged activity minus the residual artifact obtained during the artifact reduction sub-procedure 51 or 55) to a preset multiple (for example, eight) of the magnitude of the residual artifact. If the magnitude of the corrected stimulated activity is too small, the system fails the residual artifact test since it is unable to sufficiently reduce the artifact. A residual artifact test failure may indicate a device malfunction or a physiological anomaly such as fusion events. To determine the reason for the test failure, the controller restarts the procedure by initializing the stimulus pulse amplitude to 3.75 V and looping back to the initial artifact reduction 51 operation. If the system fails the residual artifact test for more than a predetermined number of consecutive attempts (for example, two), the controller terminates the procedure by setting the stimulus pulse amplitude to a safe level (for example, 7.5 V) and jumping to the end signature 57 sub-procedure. If the procedure terminates in this manner in a predetermined number (for example, four) of consecutive attempts, the controller 11 prevents further attempts by disabling the procedure. Only intervention by an external programmer over the telemetry link will re-activate the procedure. If the averaged activity signal passes the residual artifact test, software derives the stimulated activity threshold value by subtracting the residual artifact found in the last residual artifact determination operation (block 63 of FIG. 4) from the averaged activity and multiplying the result by a predetermined fractional factor. This factor defines the minimum activity signal that will indicate a successful stimulation of the heart, taking into consideration the average signal level and the detected noise level (the residual artifact), and setting the threshold level between them. In the preferred embodiment of the invention, the value of the factor is either 50 percent or 25 percent, respectively, for signals sensed in the bipolar and unipolar configurations to compensate for the difference in waveforms.

After the successful completion of initial stimulated activity threshold block 53 (FIG. 3), the controller 11 performs the vario 54 sub-procedure to determine the stimulation pulse amplitude normally capable of giving rise to a response by the heart. The beginning stimulus pulse amplitude for the vario operation is the same as the amplitude used when performing the initial stimulated activity threshold 53 sub-procedure. For each vario cardiac cycle, the controller 11 measures the activity as described previously. If the stimulus pulse succeeds in stimulating a cardiac response, the controller decreases the stimulation amplitude by a preset step size (for example, 0.1 V) for the next cardiac cycle. If the stimulus fails to evoke a response, the stimulation amplitude remains the same. After three consecutive failures, the vario operation is complete and the controller increases the stimulation amplitude by a preset voltage margin (0.6 V in the preferred embodiment of the invention) and the device begins performing the final artifact reduction 55 sub-procedure. The vario operation will also terminate without failing to generate a cardiac response if the software decrements the stimulation amplitude below a predetermined minimum stimulation level, such as 0.5 V.

If the device 1 detects a noise cycle during the vario operation, software restarts the stepwise vario function by initializing the stimulus pulse amplitude to the original level for the current sub-procedure. This is done to avoid generating pulses which are inadequate to stimulate the heart during continuing noise cycles. To limit the time a patient is subject to the possibly inadequate stimulus pulse amplitudes tested within the stepwise vario operation, software limits the number of cardiac cycles in which natural activity inhibits pacing or noise occurs during the sub-procedure. If the number of such cardiac cycles surpasses this limit (for example, 32 cycles), the controller 11 terminates the procedure by jumping to the end signature 57 sub-procedure after setting the stimulus pulse amplitude to the value determined in the last vario procedure or, if the device is performing the procedure because of a failure to stimulate the heart, to a safe level (for example, 7.5 V).

After performing the vario 54 operation, software controls the final artifact reduction 55 sub-procedure to minimize the magnitude of the polarization artifact after the pulse amplitude is set to the newly determined stimulation threshold plus margin value. Operations of the final (block 55) and initial (block 51) artifact reduction sub-procedures are identical except for possible differences in the generated stimulation pulse amplitudes.

In the final stimulated activity threshold 56 sub-procedure, the device determines the stimulated activity threshold value for cardiac signals stimulated from pulses having the newly determined stimulation amplitude. Other than possible changes in stimulation pulse amplitude, the final (56) and initial (53) stimulated activity threshold sub-procedures are the same.

End signature 57 sub-procedure provides notification to anyone monitoring the cardiac signal that the FIG. 3 operation is ending. The start (50) and end (57) signature operations are the same except for possible differences in the stimulus amplitude. A successful vario 54 operation will have set the stimulation amplitude to the stimulation threshold plus margin value. A procedure failure such as too large a stimulus threshold value, or failure of the residual artifact test, results in a safe default stimulation amplitude.

The device performs the stimulated potential sampling 58 sub-procedure only if the preceding sub-procedures and tests succeeded. If the automatic stimulus amplitude function is enabled, the stimulation amplitude is the stimulation threshold plus margin value determined in the vario 54 sub-procedure. The stimulated potential sampling sub-procedure 58, interfaces the device 1 to any number of different end uses which require accurate sensing of stimulated potentials (i.e., wherein the stimulated potential artifact has been reduced or eliminated). Examples of such end uses are heart rejection monitors and/or heart rejection drug dosimeters, rate-responsive cardiac pacing wherein the rate-responsive decision parameter is based on characteristics of cardiac depolarization or repolarization, and automatic stimulation threshold tracking wherein stimulus polarization artifact reduction is required to permit accurate evaluation of the stimulated response of the heart.

Considering the device 1 as part of an automatic threshold tracking apparatus, the stimulation potential sampling procedure 58 monitors the activity of the stimulated potential in the manner previously described to determine whether the stimulus amplitude (stimulation threshold plus margin) remains sufficient to activate the heart. While performing automatic threshold tracking, the device 1 reduces the stimulation rate to a non-overdrive rate during the stimulated potential sampling 58 sub-procedure. This operation may occur on every stimulated cardiac cycle or only on selected cycles, as selected by the external programmer. After a single failure to generate a cardiac response, the controller 11 increases the stimulation rate by a predetermined amount (for example, 15 bpm) in case the device incorrectly classifies a fusion event as the failure to stimulate the heart. After two consecutive failures, the controller increases the stimulation rate by a predetermined amount further (for example, to a total increase of 25 bpm) and delivers a backup stimulation pulse in the manner described previously. After three consecutive failures, the controller delivers a backup stimulation pulse, increases the stimulation pulse amplitude to a safe level, and restarts the polarization artifact reduction procedure.

Although the invention is described with reference to particular embodiments, it is to be understood that such embodiments are merely illustrative of the application of the principles of the invention. Numerous modifications may be made therein and other arrangements may be devised without departing from the spirit and scope of the invention.

We claim:

1. An apparatus, adapted to be implanted in a patient, for electrically stimulating the heart and analyzing the heart's stimulated response, comprising:

means for generating triphasic cardiac stimulation pulses having a first and third phase of one polarity and a second phase of the opposite polarity, means for timing the generation of said triphasic cardiac stimulation pulses so that at least one pulse occurs during the refractory period of the heart in each of a plurality of cardiac cycles, means operative during the refractory period of the heart for measuring a stimulation polarization artifact resulting from the generation of said triphasic cardiac stimulation pulses, and means operative to adjust the amplitude and polarity of the current flow during at least one phase of each of said triphasic cardiac stimulation pulses for reducing the amplitude of said stimulation polarization artifact.

2. An apparatus in accordance with claim 1, wherein during a period lasting from ten to fifty milliseconds following said stimulation pulse, said measuring means derives a parameter characterizing the polarity of the stimulation polarization artifact, and wherein said reducing means adjusts the current flow by varying the duration of the first phase of said triphasic cardiac stimulation pulse.

3. An apparatus in accordance with claim 2, wherein the amplitude of the stimulation polarization artifact is characterized as a residual artifact, after adjustment of its amplitude and polarity of current flow, and further comprising:

means for determining when the residual artifact is excessive in comparison to the amplitude of the heart's stimulated response, and means for generating a signal representative of the excessive residual artifact condition.

4. An apparatus in accordance with claim 3, wherein said pulse generating means also generates suprathreshold stimulation pulses which initiate said cardiac cycles, further comprising:

means, including a sensing gain control, for measuring the amplitude of the heart's stimulated response to said suprathreshold stimulation pulses, and means for adjusting said sensing gain control to limit the measured amplitude of the heart's response to a predetermined range of values.

5. An apparatus in accordance with claim 2, further comprising:

means for measuring the values of underlying physiological signals occurring concurrently with said stimulation polarization artifact during the refractory period, and means for correcting said stimulation polarization artifact to remove said underlying physiological signal values therefrom.

6. An apparatus in accordance with claim 5, wherein the amplitude of the stimulation polarization artifact is characterized as a residual artifact, after adjustment of its amplitude and polarity of current flow, and further comprising:

means for determining when the residual artifact is excessive in comparison to the amplitude of the heart's stimulated response, and means for generating a signal representative of the excessive residual artifact condition.

7. An apparatus in accordance with claim 6, wherein said pulse generating means also generates suprathreshold stimulation pulses which initiate said cardiac cycles, further comprising:

means, including a sensing gain control, for measuring the amplitude of the heart's stimulated response to said suprathreshold stimulation pulses, and means for adjusting said sensing gain control to limit the measured amplitude of the heart's response to a predetermined range of values.

8. An apparatus in accordance with claim 1, further comprising:

means for measuring the values of underlying physiological signals occurring concurrently with said stimulation polarization artifact during the refractory period, and means for correcting said stimulation polarization artifact to remove said underlying physiological signal values therefrom.

9. An apparatus in accordance with claim 8, wherein the amplitude of the stimulation polarization artifact is characterized as a residual artifact, after adjustment of its amplitude and polarity of current flow, and further comprising:

means for determining when the residual artifact is excessive in comparison to the amplitude of the heart's stimulated response, and means for generating a signal representative of the excessive residual artifact condition.

10. An apparatus in accordance with claim 9, wherein said pulse generating means also generates suprathreshold stimulation pulses which initiate said cardiac cycles, further comprising:

means, including a sensing gain control, for measuring the amplitude of the heart's stimulated response to said suprathreshold stimulation pulses, and means for adjusting said sensing gain control to limit the measured amplitude of the heart's response to a predetermined range of values.

11. An apparatus in accordance with claim 1, wherein the amplitude of the stimulation polarization artifact is characterized as a residual artifact, after adjustment of its amplitude and polarity of current flow, and further comprising:

means for determining when the residual artifact is excessive in comparison to the amplitude of the heart's stimulated response, and means for generating a signal representative of the excessive residual artifact condition.

12. An apparatus in accordance with claim 11, wherein said pulse generating means also generates suprathreshold stimulation pulses which initiate said cardiac cycles, further comprising:

means, including a sensing gain control, for measuring the amplitude of the heart's stimulated response to said suprathreshold stimulation pulses, and means for adjusting said sensing gain control to limit the measured amplitude of the heart's response to a predetermined range of values.

13. An apparatus in accordance with claim 1, wherein said pulse generating means also generates suprathreshold stimulation pulses which initiate said cardiac cycles, further comprising:

means, including a sensing gain control, for measuring the amplitude of the heart's stimulated response to said suprathreshold stimulation pulses, and means for adjusting said sensing gain control to limit the measured amplitude of the heart's response to a predetermined range of values.

14. A method of electrically stimulating a patient's heart and analyzing the heart's stimulated response, comprising the steps of:

generating triphasic cardiac stimulation pulses having first and third phases of one polarity and a second phase of the opposite polarity, timing the generation of said triphasic cardiac stimulation pulses so that at least one pulse occurs during the refractory period of the heart in each of a plurality of cardiac cycles, measuring a stimulation polarization artifact resulting from the generation of said triphasic cardiac stimulation pulses during the refractory period of the heart, and adjusting the amplitude and polarity of the current flow during at least one phase of said triphasic cardiac stimulation pulses to reduce the amplitude of said stimulation polarization artifact.

15. A method in accordance with claim 14, wherein during a period lasting from ten to fifty milliseconds following said stimulation pulse, a parameter characterizing the polarity of the stimulation polarization artifact is derived, and wherein said current flow is adjusted by varying the duration of said triphasic cardiac stimulation pulse.

16. A method in accordance with claim 15, wherein after adjustment of the stimulation polarization artifact's amplitude and polarity of current flow, the amplitude of the stimulation polarization artifact is characterized as a residual artifact, further comprising the steps of:

detecting the condition in which the residual artifact amplitude is excessive in comparison to the amplitude of the heart's stimulated response, and generating a signal representative of this condition.

17. A method in accordance with claim 15, further comprising the steps of:

measuring the values of underlying physiological signals occurring concurrently with said stimulation polarization artifact during the refractory period, and correcting said stimulation polarization artifact to remove said underlying physiological signal values therefrom.

18. A method in accordance with claim 17, wherein after adjustment of the stimulation polarization artifact's amplitude and polarity of current flow, the amplitude of the stimulation polarization artifact is characterized as a residual artifact, further comprising the steps of:

detecting the condition in which the residual artifact amplitude is excessive in comparison to the amplitude of the heart's stimulated response, and generating a signal representative of this condition.

19. A method in accordance with claim 14, further comprising the steps of:

measuring the values of underlying physiological signals occurring concurrently with said stimulation polarization artifact during the refractory period, and correcting said stimulation polarization artifact to remove said underlying physiological signal values therefrom.

20. A method in accordance with claim 19, wherein after adjustment of the stimulation polarization artifact's amplitude and polarity of current flow, the amplitude of the stimulation polarization artifact is characterized as a residual artifact, further comprising the steps of:

detecting the condition in which the residual artifact amplitude is excessive in comparison to the amplitude of the heart's stimulated response, and generating a signal representative of this condition.

21. A method in accordance with claim 14, wherein after adjustment of the stimulation polarization artifact's amplitude and polarity of current flow, the amplitude of the stimulation polarization artifact is characterized as a residual artifact, further comprising the steps of:

detecting the condition in which the residual artifact amplitude is excessive in comparison to the amplitude of the heart's stimulated response, and generating a signal representative of this condition.

22. An apparatus, adapted to be implanted in a patient, for electrically stimulating the heart and analyzing the heart's stimulated response, comprising:

means for generating triphasic cardiac stimulation pulses having a first and third phase of one polarity and a second phase of the opposite polarity, means for timing the generation of said triphasic cardiac stimulation pulses so that at least one pulse occurs during the refractory period of the heart in each of a plurality of cardiac cycles, means operative during the refractory period of the heart for measuring a stimulation polarization artifact resulting from the generation of said triphasic cardiac stimulation pulses, wherein during a period lasting from ten to fifty milliseconds following said stimulation pulse, said measuring means derives a parameter characterizing the polarity of the stimulation polarization artifact, means operative to adjust the amplitude and polarity of the current flow during at least one phase of each of said triphasic cardiac stimulation pulses for reducing the amplitude of said stimulation polarization artifact, means for measuring the values of underlying physiological signals occurring concurrently with said stimulation polarization artifact during the refractory period, and means for correcting said stimulation polarization artifact to remove said underlying physiological signal values therefrom.

23. An apparatus in accordance with claim 22, wherein the amplitude of the stimulation polarization artifact is characterized as a residual artifact, after adjustment of its amplitude and polarity of current flow, and further comprising:

means for determining when the residual artifact is excessive in comparison to the amplitude of the heart's stimulated response, and means for generating a signal representative of the excessive residual artifact condition.

24. An apparatus in accordance with claim 23, wherein said pulse generating means also generates suprathreshold stimulation pulses which initiate said cardiac cycles, and further comprising:

means, including a sensing gain control, for measuring the amplitude of the heart's stimulated response to said suprathreshold stimulation pulses, and means for adjusting said sensing gain control to limit the measured amplitude of the heart's response to a predetermined range of values.

25. An apparatus in accordance with claim 22, wherein said pulse generating means also generates suprathreshold stimulation pulses which initiate said cardiac cycles, and further comprising:

means, including a sensing gain control, for measuring the amplitude of the heart's stimulated response to said suprathreshold stimulation pulses, and means for adjusting said sensing gain control to limit the measured amplitude of the heart's response to a predetermined range of values.

26. A method of electrically stimulating a patient's heart and analyzing the heart's stimulated response, comprising the steps of:

generating triphasic cardiac stimulation pulses having first and third phases of one polarity and a second phase of the opposite polarity, timing the generation of said triphasic cardiac stimulation pulses so that at least one pulse occurs during the refractory period of the heart in each of a plurality of cardiac cycles, measuring a stimulation polarization artifact resulting from the generation of said triphasic cardiac stimulation pulses during a period lasting from ten to fifty milliseconds following said stimulation pulse within the refractory period of the heart, deriving a parameter characterizing the polarity of the stimulation polarization artifact, and adjusting the amplitude and polarity of the current flow during at least one phase of each of said triphasic cardiac stimulation pulses to reduce the amplitude of said stimulation polarization artifact.

27. A method in accordance with claim 26, further comprising the steps of:

measuring the values of underlying physiological signals occurring concurrently with said stimulation polarization artifact during the refractory period, and correcting said stimulation polarization artifact to remove said underlying physiological signal values therefrom.

28. A method in accordance with claim 27, wherein after adjustment of the stimulation polarization artifact's amplitude and polarity of current flow, the amplitude of the stimulation polarization artifact is characterized as a residual artifact, and further comprising the steps of:

detecting the condition in which the residual artifact is excessive in comparison to the amplitude of the heart's stimulated response, and generating a signal representative of this condition.

29. A method in accordance with claim 26, wherein after adjustment of the stimulation polarization artifact's amplitude and polarity of current flow, the amplitude of the stimulation polarization artifact is characterized as a residual artifact, and further comprising the steps of:

detecting the condition in which the residual artifact is excessive in comparison to the amplitude of the heart's stimulated response, and generating a signal representative of this condition.

* * * * *